(12) United States Patent
Oota et al.

(10) Patent No.: US 9,023,469 B2
(45) Date of Patent: May 5, 2015

(54) BASIC ZINC CYANURATE FINE PARTICLES, AND METHOD FOR PRODUCING SAME

(75) Inventors: Isao Oota, Chiba (JP); Masaki Oiwamoto, Toyama (JP); Takeshi Suwa, Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 135 days.

(21) Appl. No.: 13/806,854

(22) PCT Filed: Jun. 23, 2011

(86) PCT No.: PCT/JP2011/064451
§ 371 (c)(1),
(2), (4) Date: Dec. 26, 2012

(87) PCT Pub. No.: WO2011/162353
PCT Pub. Date: Dec. 29, 2011

(65) Prior Publication Data
US 2013/0108871 A1  May 2, 2013

(30) Foreign Application Priority Data

Jun. 24, 2010 (JP) ................................ 2010-144189

(51) Int. Cl.
*B82Y 30/00* (2011.01)
*C07D 251/32* (2006.01)
*C01C 3/14* (2006.01)

(52) U.S. Cl.
CPC .............. *C07D 251/32* (2013.01); *B82Y 30/00* (2013.01); *C01C 3/14* (2013.01); *C01P 2002/72* (2013.01); *C01P 2002/88* (2013.01); *C01P 2004/04* (2013.01); *C01P 2004/10* (2013.01); *C01P 2004/54* (2013.01); *C01P 2004/62* (2013.01); *C01P 2004/64* (2013.01); *C01P 2006/12* (2013.01); *C01P 2006/22* (2013.01); *Y10S 977/773* (2013.01); *Y10S 977/788* (2013.01); *Y10S 977/896* (2013.01); *Y10T 428/2982* (2015.01)

(58) Field of Classification Search
USPC ........ 428/402; 420/513; 106/18.27; 544/181; 977/773, 788, 896
IPC ............ B82Y 30/00; C07D 251/32; C01C 3/14
See application file for complete search history.

(56) References Cited

U.S. PATENT DOCUMENTS

| 4,329,381 A | 5/1982 | Eschwey et al. |
| 4,507,270 A | 3/1985 | Harth et al. |
| 5,147,912 A * | 9/1992 | Moore ........................... 524/101 |

FOREIGN PATENT DOCUMENTS

| JP | 45 19518 | 7/1970 |
| JP | 54 123145 | 9/1979 |
| JP | 59 31779 | 2/1984 |
| JP | 5 9383 | 1/1993 |
| JP | 8 157595 | 6/1996 |
| JP | 2003-138082 | 5/2003 |
| WO | 93 06155 | 4/1993 |
| WO | WO93/06155 | * 4/1993 |

OTHER PUBLICATIONS

International Search Report Issued Sep. 20, 2011 in PCT/JP11/64451 Filed Jun. 23, 2011.
Office Action issued Dec. 10, 2014 in corresponding Japanese Patent Application No. 2012-521536.

* cited by examiner

*Primary Examiner* — Leszek Kiliman
(74) *Attorney, Agent, or Firm* — Oblon, McClelland, Maier & Neustadt, L.L.P.

(57) ABSTRACT

Basic zinc cyanurate fine particles are produced by subjecting a mixed slurry to wet dispersion using a dispersion medium at a temperature in the range of 5 to 55° C., the mixed slurry being formed by blending water, cyanuric acid, and at least one component selected from zinc oxide and basic zinc carbonate such that the cyanuric acid concentration is 0.1 to 10.0 mass % with respect to water.

18 Claims, 5 Drawing Sheets

BASIC ZINC CYANURATE FINE PARTICLES, AND METHOD FOR PRODUCING SAME

TECHNICAL FIELD

This invention relates to basic zinc cyanurate fine particles, and a method for producing the basic zinc cyanurate fine particles.

BACKGROUND ART

As a method for producing zinc cyanurate, which is known as a corrosion inhibiting coating agent for an iron-based metal surface, a disclosure is made of a method which comprises reacting zinc oxide and cyanuric acid in boiling water (see Patent Document 1). Also disclosed is a technology for producing basic zinc cyanurate particles by exerting a shearing action on a paste by means of a pin disc mill or a blade mill while heating the paste at 50 to 250° C., the paste being formed by mixing zinc oxide and cyanuric acid in a proportion of 10 to 80% by weight (based on the paste) such that they form a kneadable paste at as low a water content as possible (see Patent Document 2).

PRIOR ART DOCUMENTS

Patent Documents

[Patent Document 1] JP-A-54-123145
[Patent Document 2] JP-A-59-31779

SUMMARY OF THE INVENTION

Problems to be Solved by the Invention

However, the zinc cyanurates obtained by the production methods described in the above-mentioned Patent Document 1 and Patent Document 2 are relatively large ones with an average particle diameter of 10 μm or more, and finer zinc cyanurate is desired.

A challenge for the present invention is to solve the above-described problem of the conventional technologies, and an object of the invention is to provide basic zinc cyanurate fine particles, and a method for producing the zinc cyanurate fine particles.

Means for Solving the Problems

The basic zinc cyanurate fine particles of the present invention, which solve the above-mentioned problem, are characterized by having an average particle diameter $D_{50}$, as measured by the laser diffraction method, of 80 to 900 nm and a specific surface area of 20 to 100 $m^2/g$.

The basic zinc cyanurate fine particles are preferably produced by subjecting a mixed slurry to wet dispersion using a dispersion medium at a temperature in the range of 5 to 55° C., the mixed slurry being formed by blending water, cyanuric acid, and at least one component selected from zinc oxide and basic zinc carbonate such that a cyanuric acid concentration is 0.1 to 10.0 mass % with respect to water.

A method for producing basic zinc cyanurate fine particles according to the present invention is characterized in that the basic zinc cyanurate fine particles are produced by subjecting a mixed slurry to wet dispersion using a dispersion medium at a temperature in the range of 5 to 55° C., the mixed slurry being formed by blending water, cyanuric acid, and at least one component selected from zinc oxide and basic zinc carbonate such that a cyanuric acid concentration is 0.1 to 10.0 mass % with respect to water.

The basic zinc cyanurate fine particles preferably have an average particle diameter $D_{50}$, as measured by the laser diffraction method, of 80 to 900 nm and a specific surface area of 20 to 100 $m^2/g$.

The dispersion medium is preferably at least one medium selected from stabilized zirconia beads, vitreous silica beads, soda-lime glass beads, and alumina beads, all beads having a diameter of 0.1 to 10 mm.

Effects of the Invention

According to the present invention, fine basic zinc cyanurate can be provided. Thus, it is preferred for uses requiring transparency. According to the method for producing basic zinc cyanurate of the present invention, fine basic zinc cyanurate particles can be produced at a low temperature of 5 to 55° C. Moreover, acicular basic zinc cyanurate fine particles can be produced.

MODE FOR CARRYING OUT THE INVENTION

Figure 1:
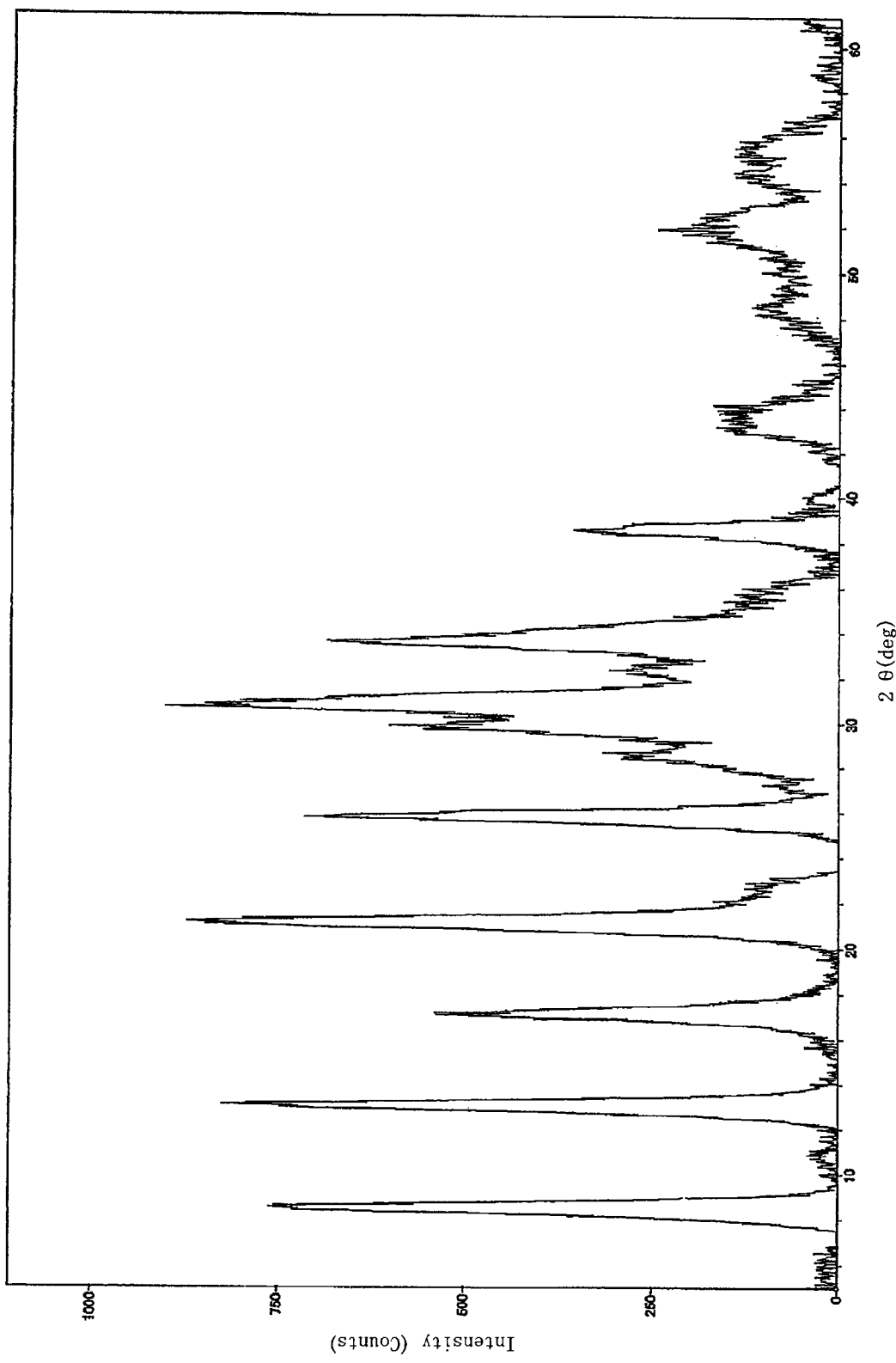
[FIG. 1] is an XRD diffraction pattern of Example 1.

The method for producing basic zinc cyanurate fine particles according to the present invention comprises subjecting a mixed slurry to wet dispersion using a dispersion medium at a temperature in the range of 5 to 55° C., the mixed slurry being formed by blending water, cyanuric acid, and at least one component selected from zinc oxide and basic zinc carbonate such that a cyanuric acid concentration is 0.1 to 10.0 mass % with respect to water.

First, cyanuric acid, water, and at least one component selected from zinc oxide and basic zinc carbonate are blended such that the cyanuric acid concentration is 0.1 to 10.0 mass %, preferably 0.1 to 5.0 mass %, with respect to water, thereby preparing a mixed slurry. If the concentration of cyanuric acid with respect to water is higher than 10 mass %, the slurry viscosity becomes so high that the slurry is pasty. Thus, when wet dispersion using a dispersion medium is performed in a subsequent stage, the dispersion medium does not move. If the concentration of cyanuric acid with respect to water is lower than 0.1 mass %, productivity is poor and the outcome is not favorable.

The ratio between cyanuric acid and at least one component selected from zinc oxide and basic zinc carbonate is not restricted. However, the total amount (calculated as zinc oxide) of zinc oxide and basic zinc carbonate/cyanuric acid, expressed as molar ratio, is preferably 1.0 to 5.0, more preferably 2.0 to 3.0. If the amount as zinc oxide/cyanuric acid is higher than 5.0 or lower than 1.0, there will be a tendency for zinc oxide, basic zinc carbonate or cyanuric acid, which has not contributed to the reaction, to remain in a large amount.

Then, the resulting mixed slurry is subjected to wet dispersion using a dispersion medium at a temperature in the range of 5 to 55° C. By so doing, at least one component selected from zinc oxide and basic zinc carbonate is reacted with cyanuric acid to produce basic zinc cyanurate fine particles.

The wet dispersion is carried out using the dispersion medium. By performing the wet dispersion using the dispersion medium, mechanical energy generated by the collision of the dispersion medium enables cyanuric acid and at least one component selected from zinc oxide and basic zinc carbonate to be subjected to a mechanochemical reaction. The mechanochemical reaction refers to a reaction in which mechanical energy is imparted to zinc oxide, basic zinc carbonate, or cyanuric acid from many directions by the collision of the dispersion medium to cause a chemical reaction.

Examples of the dispersion medium are stabilized zirconia beads, vitreous silica beads, soda-lime glass beads, alumina beads, and mixtures thereof. In consideration of contamination which occurs upon mutual collision of the dispersion medium, resulting in the crushing of the dispersion medium, it is preferred to use stabilized zirconia beads as the dispersion medium. The size of the dispersion medium is, for example, 0.1 to 10 mm in diameter, preferably 0.5 to 2.0 mm in diameter. If the diameter of the dispersion medium is less than 0.1 mm, the energy of the grinding medium colliding mutually is so low that the mechanochemical reactivity tends to weaken. If the diameter of the dispersion medium is larger than 10 mm, the energy of mutual collision of the dispersion medium is so great that the dispersion medium is crushed, leading to considerable contamination. This is an undesirable situation.

A device for performing wet dispersion using the dispersion medium is not limited, if it allows a process in which the mixed slurry is added to a container containing the dispersion medium, and then stirred to cause collision of the dispersion medium with zinc oxide, basic zinc carbonate, and cyanuric acid, whereby zinc oxide and/or basic zinc carbonate and cyanuric acid can be mechanochemically reacted. Examples of the device are a sand grinder, a horizontal bead mill, an attritor, and a pearl mill (a product of Ashizawa Finetech Ltd.). The number of revolutions, the reaction time, etc. of the device for stirring the dispersion medium may be adjusted, as appropriate, in conformity with the desired particle diameter, etc.

The wet dispersion needs to be performed at 5 to 55° C., preferably 5 to 45° C. When the wet dispersion is carried out at a temperature higher than 55° C., cyanuric acid dissolves in water, and the dissolved cyanuric acid may rapidly react with zinc oxide or basic zinc carbonate to promote particle growth. Probably under this action, basic zinc cyanurate produced has a large particle diameter, as will be shown in Comparative Examples to be presented later. By performing wet dispersion at a low temperature equal to or lower than 45° C., particularly small particles are formed. For example, fine particles having an average particle diameter $D_{50}$, as measured by the laser diffraction method, of 500 nm or less can be produced. Since the fine particles can be produced at such a low temperature, production can be done using a heat-susceptible device formed from resin.

With a method applying a shearing action by a pin disc mill or a blade mill as in Patent Document 2, rather than wet dispersion using a dispersion medium as in the present invention, the shearing member collides with zinc oxide, basic zinc carbonate and cyanuric acid only in one direction, and no mechanochemical reaction takes place. Probably for this reason, it is impossible to obtain basic zinc cyanurate having a small particle diameter as done in the present invention.

As described above, basic zinc cyanurate fine particles are obtained by the production method which comprises subjecting the mixed slurry to wet dispersion using the dispersion medium at a temperature in the range of 5 to 55° C., the mixed slurry being formed by blending water, cyanuric acid, and at least one component selected from zinc oxide and basic zinc carbonate such that the cyanuric acid concentration is 0.1 to 10.0 mass % with respect to water. The resulting basic zinc cyanurate fine particles have an average particle diameter $D_{50}$, as measured by the laser diffraction method, of 80 to 900 nm, preferably 100 to 500 nm, and a specific surface area of 20 to 100 m$^2$/g, preferably 30 to 80 m$^2$/g. That is, the particles have a small particle diameter and a large specific surface area. Even if conventional basic zinc cyanurate having a large particle diameter in comparison with the basic zinc cyanurate fine particles of the present invention is pulverized with a crusher such as a counter jet mill, it cannot be converted into fine zinc cyanurate having an average particle diameter $D_{50}$, as measured by the laser diffraction method, of 80 to 900 nm, like the zinc cyanurate of the present invention.

The basic zinc cyanurate fine particles obtained by the above production method are not spherical, but can be acicular or plate-shaped, namely, elongated fine particles, as shown in Examples to be offered later. Such basic zinc cyanurate fine particles have, for example, a primary particle diameter, as observed under a transmission electron microscope, of 100 to 800 nm on the major axis and 10 to 60 nm on the minor axis, the major axis/minor axis ratio (axial ratio) being 5 to 25.

The above-mentioned basic zinc cyanurate fine particles of the present invention can be used as a high-performance corrosion inhibiting coating agent for a metal surface, like the conventional zinc cyanurate described in Patent Document 1 or the like. Furthermore, the basic zinc cyanurate fine particles of the present invention can be used as a crystal nucleating agent for controlling the crystallinity of a crystallizable polymer such as polypropylene, polylactic acid, or polyethylene, or as a filler for a polymeric material.

A basic zinc cyanurate slurry containing the basic zinc cyanurate fine particles obtained by the production method described above may be used as such, or a powdery product formed by drying the slurry may be used. Besides, the basic zinc cyanurate fine particles may be dissolved or dispersed in a solvent to form a crystal nucleating agent composition or a filler composition.

Since the basic zinc cyanurate fine particles of the present invention have a small particle diameter, they can serve as a crystal nucleating agent or a filler which are satisfactory in transparency. Thus, they can be used preferably as a crystal nucleating agent for a polymer or a filler which are required to be transparent.

EXAMPLES

The present invention will be described in further detail based on the Examples and Comparative Examples to be presented below. However, the present invention is in no way limited by these examples.

(Measuring Devices)

Analyses in the Examples and the Comparative Examples were made using the following devices and conditions:

Observation by transmission electron microscope: JEM-1010 (produced by JEOL), applied voltage 100 KV Measurement of particle diameter by the laser diffraction method: SALD-7000 (produced by Shimadzu Corp.), 1 g of sample was diluted 1:200 with pure water, and measured.

Measurement of specific surface area: Surface area measuring device Monosorb (produced by Yuasa Ionics Co., Ltd.) by the nitrogen adsorption method Gravimetric analysis: Sample (about 2 g) was placed in a porcelain crucible, precisely weighed, and then dried at 110° C. The solid content was calculated from the dry weight.

Identification by X-ray powder diffraction: Powder X-ray diffractometer RINT Ultima (produced by Rigaku Corporation)

Elemental analysis: Full automatic elemental analyzer CHNS/O Analyzer 2400 (produced by Perkin Elmer Co., Ltd.)

Example 1

Figure 2:
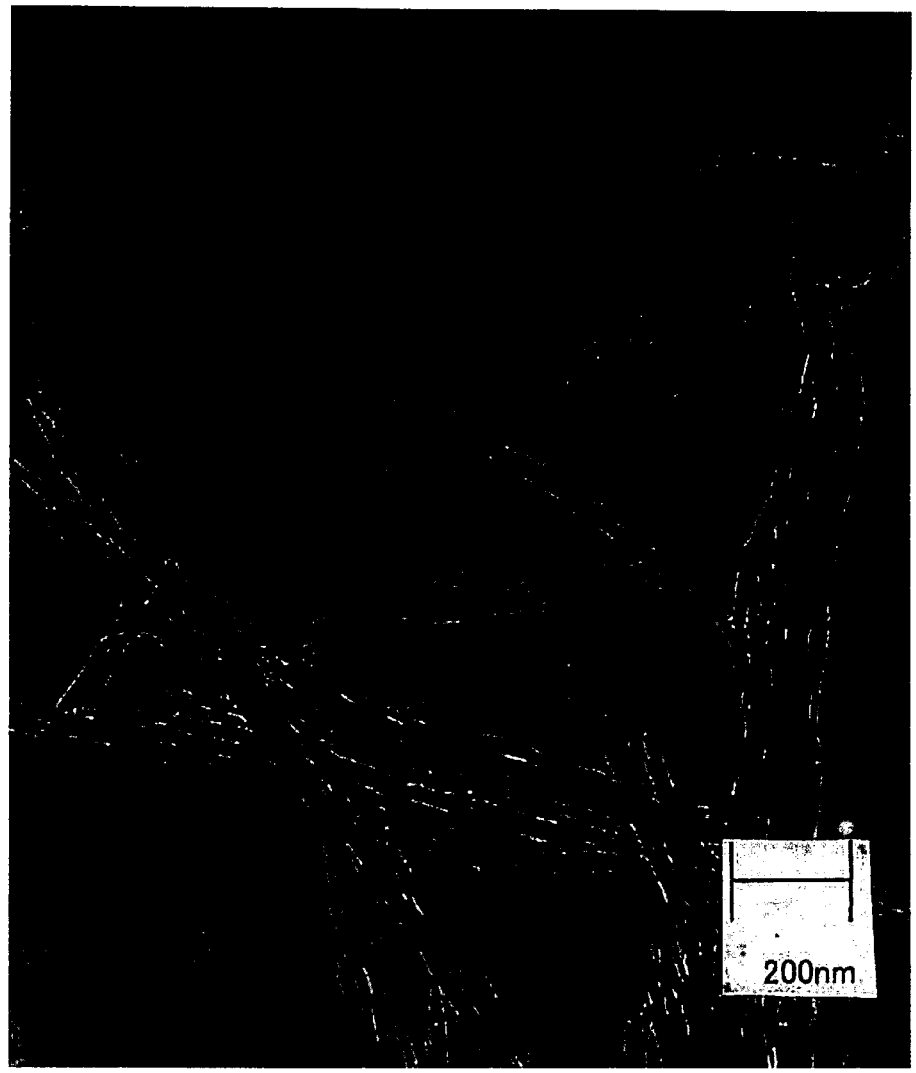
[FIG. 2] is a TEM photograph of Example 1.

A batchwise sand grinder container having a volume of 1 L and having an internal wall of urethane resin was charged with 1140 g of stabilized zirconia grinding beads having a diameter of 1 mm, and 300 g of pure water. With the sand grinder container being cooled by a chiller at −5° C., a stirring disk was rotated at 500 rpm, and 5.9 g of a cyanuric acid powder (produced by Nissan Chemical Industries, Ltd.) was charged into the system. Then, with the sand grinder container being cooled by the chiller at −5° C., the stirring disk was rotated at 500 rpm, and 9.3 g of a zinc oxide powder (JIS-2 grade zinc oxide produced by SAKAI CHEMICAL INDUSTRY CO., LTD.) was charged into the system. The zinc oxide/cyanuric acid molar ratio was 2.5, and the cyanuric acid concentration with respect to water was 2.0 mass %. After charging of the zinc oxide powder, the sand grinder container was cooled for 12 hours by the chiller at −5° C. and, during this process, the stirring disk was rotated at 500 rpm to disperse the system. The slurry temperature at this time was 9° C. By this treatment, a white slurry having a pH of 7.1, an electric conductivity of 84 μS/cm, and a solid content when dried at 110° C. of 4.8 mass % was obtained in an amount of 310 g. The elemental analysis of a 110° C. dried powder of the resulting white slurry showed 10.37 mass % carbon, 1.35 mass % hydrogen, 12.05 mass % nitrogen, and 28.20 mass % oxygen. This 110° C. dried powder was pyrolyzed at 1000° C. to form zinc oxide, and its weight was measured to determine the amount of Zn as the active ingredient in the 110° C. dried powder. The amount of the active ingredient was found to be 48.03 mass %. The X-ray powder diffraction analysis of the 110° C. dried powder was made. As shown in FIG. 1, no diffraction peaks attributed to the staring cyanuric acid and zinc oxide were observed, and diffraction peaks of basic zinc cyanurate were observed. Based on these results, it was determined that the 110° C. dried powder was basic zinc cyanurate represented by $Zn_5(C_3N_3O_3)_2(OH)_3 \cdot 3H_2O$. Fine particles contained in the resulting white slurry comprised basic zinc cyanurate having a major axis length of 100 to 200 nm and a minor axis length of 10 to 15 nm according to transmission electron microscopic observation, an average particle diameter $D_{50}$, by laser diffraction particle diameter measurement, of 103 nm, and a specific surface area Sw, after drying at 70° C., of 59 m$^2$/g. The results are shown in Table 1. The axial ratio (major axis/minor axis) in Table 1 was the average value of 20 of the basic zinc cyanurate fine particles. A photograph of the fine particles based on transmission electron microscopic observation is shown in FIG. 2.

Example 2

A batchwise sand grinder container having a volume of 1 L and having an internal wall of urethane resin was charged with 1140 g of stabilized zirconia grinding beads having a diameter of 1 mm, and 300 g of pure water. With the sand grinder container being cooled by a chiller at −5° C., a stirring disk was rotated at 1500 rpm, and 5.9 g of a cyanuric acid powder (produced by Nissan Chemical Industries, Ltd.) was charged into the system. Then, with the sand grinder container being cooled by the chiller at −5° C., the stirring disk was rotated at 1500 rpm, and 9.3 g of a zinc oxide powder (JIS-2 grade zinc oxide produced by SAKAI CHEMICAL INDUSTRY CO., LTD.) was charged into the system. The zinc oxide/cyanuric acid molar ratio was 2.5, and the cyanuric acid concentration with respect to water was 2.0 mass %. After charging of the zinc oxide powder, the sand grinder container was cooled for 8 hours by the chiller at 0° C. and, during this process, the stirring disk was rotated at 1500 rpm to disperse the system. The slurry temperature at this time was 16° C. By this treatment, a white slurry having a pH of 7.1, an electric conductivity of 109 μS/cm, and a solid content when dried at 110° C. of 4.8 mass % was obtained in an amount of 311 g. The X-ray powder diffraction analysis of a 110° C. dried powder of the resulting white slurry showed a diffraction pattern similar to that of Example 1. Fine particles contained in the resulting white slurry comprised basic zinc cyanurate having a major axis length of 100 to 300 nm and a minor axis length of 10 to 20 nm according to transmission electron microscopic observation, an average particle diameter $D_{50}$, by laser diffraction particle diameter measurement, of 155 nm, and a specific surface area Sw, after drying at 70° C., of 49 m$^2$/g. The results are shown in Table 1.

Example 3

Figure 3:
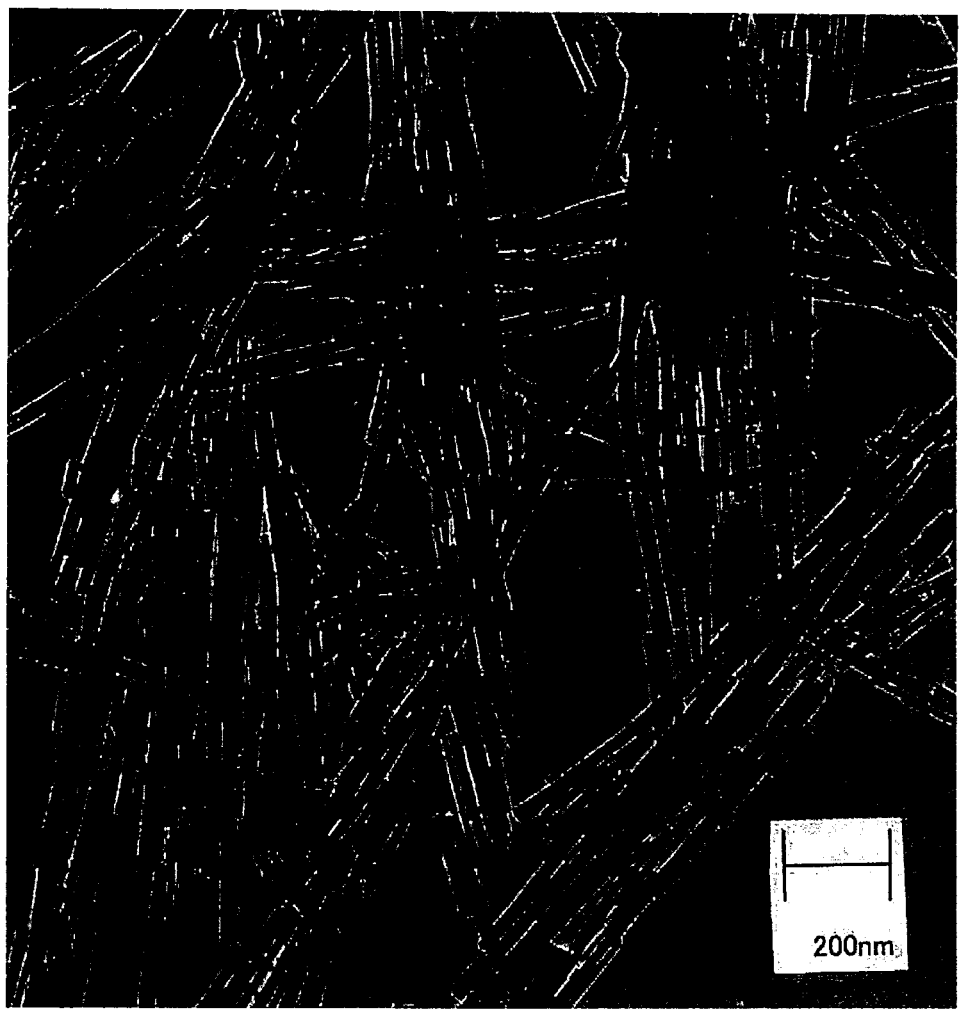
[FIG. 3] is a TEM photograph of Example 3.

A batchwise sand grinder container having a volume of 1 L and having an internal wall of urethane resin was charged with 1140 g of stabilized zirconia grinding beads having a diameter of 1 mm, and 300 g of pure water. With the sand grinder container being cooled by a chiller at −5° C., a stirring disk was rotated at 2000 rpm, and 5.9 g of a cyanuric acid powder (produced by Nissan Chemical Industries, Ltd.) was charged into the system. Then, with the sand grinder container being cooled by the chiller at −5° C., the stirring disk was rotated at 2000 rpm, and 9.3 g of a zinc oxide powder (JIS-2 grade zinc oxide produced by SAKAI CHEMICAL INDUSTRY CO., LTD.) was charged into the system. The zinc oxide/cyanuric acid molar ratio was 2.5, and the cyanuric acid concentration with respect to water was 2.0 mass %. After charging of the zinc oxide powder, the sand grinder container was cooled for 8 hours by the chiller at −5° C. and, during this process, the stirring disk was rotated at 2000 rpm to disperse the system. The slurry temperature at this time was 23° C. By this treatment, a white slurry having a pH of 7.0, an electric conductivity of 120 μS/cm, and a solid content when dried at 110° C. of 4.8 mass % was obtained in an amount of 305 g. The X-ray powder diffraction analysis of a 110° C. dried powder of the resulting white slurry showed a diffraction pattern similar to that of Example 1. Fine particles contained in the resulting white slurry comprised basic zinc cyanurate having a major axis length of 100 to 400 nm and a minor axis length of 20 to 30 nm according to transmission electron microscopic observation, an average particle diameter $D_{50}$, by laser diffraction particle diameter measurement, of 175 nm, and a specific surface area Sw, after drying at 70° C., of 32 m$^2$/g. The results are shown in Table 1. A photograph of the fine particles based on transmission electron microscopic observation is shown in FIG. 3.

Example 4

A batchwise sand grinder container having a volume of 1 L and having an internal wall of urethane resin was charged with 1140 g of stabilized zirconia grinding beads having a diameter of 1 mm, and 290 g of pure water. With the sand grinder container being cooled with tap water at 20° C., a stirring disk was rotated at 1500 rpm, and 9.2 g of a cyanuric acid powder (produced by Nissan Chemical Industries, Ltd.) was charged into the system. Then, with the sand grinder container being cooled with tap water at 20° C., the stirring disk was rotated at 1500 rpm, and 14.5 g of a zinc oxide powder (JIS-2 grade zinc oxide produced by SAKAI CHEMICAL INDUSTRY CO., LTD.) was charged into the system. The zinc oxide/cyanuric acid molar ratio was 2.5, and the cyanuric acid concentration with respect to water was 3.2 mass %. After charging of the zinc oxide powder, the sand grinder container was cooled for 10 hours with tap water at 20° C. and, during this process, the stirring disk was rotated at 1500 rpm to disperse the system. The slurry temperature at this time was 40° C. By this treatment, a white slurry having a pH of 6.8, an electric conductivity of 148 µS/cm, and a solid content when dried at 110° C. of 7.5 mass % was obtained in an amount of 300 g. The X-ray powder diffraction analysis of a 110° C. dried powder of the resulting white slurry showed a diffraction pattern similar to that of Example 1. Fine particles contained in the resulting white slurry comprised basic zinc cyanurate having a major axis length of 100 to 300 nm and a minor axis length of 20 to 30 nm according to transmission electron microscopic observation, an average particle diameter $D_{50}$, by laser diffraction particle diameter measurement, of 188 nm, and a specific surface area Sw, after drying at 70° C., of 26 $m^2/g$.

Example 5

A batchwise sand grinder container having a volume of 1 L and having an internal wall of urethane resin was charged with 1140 g of stabilized zirconia grinding beads having a diameter of 1 mm, and 290 g of pure water. A stirring disk was rotated at 1500 rpm, and 5.9 g of a cyanuric acid powder (produced by Nissan Chemical Industries, Ltd.) was charged into the system. Then, the stirring disk was rotated at 1500 rpm, and 9.3 g of a zinc oxide powder (JIS-2 grade zinc oxide produced by SAKAI CHEMICAL INDUSTRY CO., LTD.) was charged into the system. The zinc oxide/cyanuric acid molar ratio was 2.5, and the cyanuric acid concentration with respect to water was 2.0 mass %. After charging of the zinc oxide powder, the stirring disk was rotated at 1500 rpm to disperse the system for 5 hours. The slurry temperature at this time was 50° C. By this treatment, a white slurry having a pH of 8.2, an electric conductivity of 176 µS/cm, and a solid content when dried at 110° C. of 4.8 mass % was obtained in an amount of 300 g. The X-ray powder diffraction analysis of a 110° C. dried powder of the resulting white slurry showed a diffraction pattern similar to that of Example 1. Fine particles contained in the resulting white slurry comprised basic zinc cyanurate having a major axis length of 100 to 200 nm and a minor axis length of 20 to 40 nm according to transmission electron microscopic observation, an average particle diameter $D_{50}$, by laser diffraction particle diameter measurement, of 623 nm, and a specific surface area Sw, after drying at 70° C., of 25 $m^2/g$. The results are shown in Table 1.

Example 6

A batchwise sand grinder container having a volume of 1 L and having an internal wall of urethane resin was charged with 1140 g of stabilized zirconia grinding beads having a diameter of 1 mm, and 298 g of pure water. With the sand grinder container being cooled by a chiller at 10° C., a stirring disk was rotated at 2000 rpm, and 4.3 g of a cyanuric acid powder (produced by Nissan Chemical Industries, Ltd.) was charged into the system. Then, with the sand grinder container being cooled by the chiller at 10° C., the stirring disk was rotated at 1500 rpm, and 9.0 g of a basic zinc carbonate powder (zinc oxide component 74.8 mass %; produced by SAKAI CHEMICAL INDUSTRY CO., LTD.) was charged into the system. The zinc oxide-converted amount/cyanuric acid molar ratio was 2.5, and the cyanuric acid concentration with respect to water was 1.4 mass %. After charging of the zinc oxide powder, the sand grinder container was cooled for 8 hours by the chiller at 10° C. and, during this process, the stirring disk was rotated at 1500 rpm to disperse the system. The slurry temperature at this time was 30° C. By this treatment, a white slurry having a pH of 6.3, an electric conductivity of 556 µS/cm, a viscosity of 198 mPa·s, and a solid content when dried at 110° C. of 3.5 mass % was obtained in an amount of 310 g. The X-ray powder diffraction analysis of a 110° C. dried powder of the resulting white slurry showed a diffraction pattern similar to that of Example 1. Fine particles contained in the resulting white slurry comprised basic zinc cyanurate having a major axis length of 100 to 300 nm and a minor axis length of 20 to 40 nm according to transmission electron microscopic observation, an average particle diameter $D_{50}$, by laser diffraction particle diameter measurement, of 303 nm, and a specific surface area Sw, after drying at 70° C., of 30 $m^2/g$. The results are shown in Table 1.

Example 7

Figure 4:
[FIG. 4] is a TEM photograph of Example 7.

Pure water (24 kg) and 1.88 kg of a zinc oxide powder (JIS-2 grade zinc oxide produced by SAKAI CHEMICAL INDUSTRY CO., LTD.) were charged into a mixing tank having a volume of 200 L, and mixed with stirring by Disper to prepare 26 kg of a slurry having a zinc oxide-converted concentration of 7.69 mass %. A horizontal beadmill (pearl mill PM25TEX-H, produced by Ashizawa Finetech Ltd.) having an effective volume of 10.66 L and having an internal wall of urethane resin was charged with 66 kg of stabilized zirconia grinding beads having a diameter of 1 mm. After a circulating tank equipped with a chiller was charged with 144 kg of pure water, a disk of the pearl mill was rotated at a peripheral speed of 10 m/second, and pure water was circulated while being supplied to the pearl mill at a feed rate of 5 kg/minute. After start of circulation, 1.19 kg of a cyanuric acid powder (produced by Nissan Chemical Industries, Ltd.) was charged into the system. After charging of the cyanuric acid powder, the circulated slurry was adjusted by the chiller to a temperature of 32° C. Then, 24.5 kg of the zinc oxide slurry having a zinc oxide-converted concentration of 7.69 mass % was divided into 5 portions, and added over the course of 10 minutes. The zinc oxide/cyanuric acid molar ratio was 2.5, and the cyanuric acid concentration with respect to water was 0.7 mass %. Upon addition of the zinc oxide slurry, the disk of the pearl mill was rotated at a peripheral speed of 10 m/second and, during this process, the slurry was circulated for 15 hours at a feeding rate of 5 kg/min for dispersion. During this course, the circulated slurry temperature was adjusted by the chiller so as to be 32° C. By this treatment, a white slurry having a pH of 6.8, an electric conductivity of 67 µS/cm, a viscosity of 51 mPa·s, and a solid content when dried at 110° C. of 1.8 mass % was obtained in an amount of 166 kg. The X-ray powder diffraction analysis of a 110° C. dried powder of the resulting white slurry showed a diffraction pattern similar to that of Example 1. Fine particles contained in the resulting white slurry comprised basic zinc cyanurate having a major axis length of 100 to 600 nm and a minor axis length of 25 to 50 nm according to transmission electron microscopic observation, an average particle diameter $D_{50}$, by laser diffraction particle diameter measurement, of 310 nm, and a specific surface area Sw, after drying at 70° C., of 51 m²/g. The results are shown in Table 1. A photograph of the fine particles based on transmission electron microscopic observation is shown in FIG. 4.

The same procedure as in Example 7 was performed, except that a horizontal bead mill (System Zeta LMZ25, produced by Ashizawa Finetech Ltd.) having an effective volume of 10.66 L and having an internal wall of urethane resin was used instead of the pearl mill. Basic zinc cyanurate fine particles similar to those in Example 7 were obtained.

Example 8

A batchwise sand grinder container having a volume of 1 L and having an internal wall of urethane resin was charged with 1140 g of stabilized zirconia grinding beads having a diameter of 1 mm, and 290 g of pure water. A stirring disk was rotated at 1500 rpm, and 5.9 g of a cyanuric acid powder (produced by Nissan Chemical Industries, Ltd.) was charged into the system. Then, the stirring disk was rotated at 1500 rpm, and 11.2 g of a zinc oxide powder (JIS-2 grade zinc oxide produced by SAKAI CHEMICAL INDUSTRY CO., LTD.) was charged into the system. The zinc oxide/cyanuric acid molar ratio was 3.0, and the cyanuric acid concentration with respect to water was 2.0 mass %. After charging of the zinc oxide powder, the stirring disk was rotated at 1500 rpm to disperse the system for 5 hours. The slurry temperature at this time was 23° C. By this treatment, a white slurry having a pH of 7.8, an electric conductivity of 98 μS/cm, and a solid content when dried at 110° C. of 5.6 mass % was obtained in an amount of 300 g. The X-ray powder diffraction analysis of a 110° C. dried powder of the resulting white slurry showed a diffraction pattern similar to that of Example 1. Fine particles contained in the resulting white slurry comprised basic zinc cyanurate having a major axis length of 100 to 300 nm and a minor axis length of 15 to 20 nm according to transmission electron microscopic observation, an average particle diameter $D_{50}$, by laser diffraction particle diameter measurement, of 152 nm, and a specific surface area Sw, after drying at 70° C., of 40 m²/g. The results are shown in Table 1.

Comparative Example 1

A 1-liter beaker charged with 900 g of pure water was placed on a hot plate equipped with a magnet stirrer, and 18.9 g of a cyanuric acid powder (produced by Nissan Chemical Industries, Ltd.) was charged into the system with stirring by the stirrer. Then, 30.0 g of a zinc oxide powder (JIS-2 grade zinc oxide produced by SAKAI CHEMICAL INDUSTRY CO., LTD.) was charged into the system, and then the mixed slurry was stirred for 8 hours, while being held at 70° C. by the hot plate, with stirring continued using the stirrer. The zinc oxide/cyanuric acid molar ratio was 2.5, and the cyanuric acid concentration with respect to water was 2.1 mass %. The resulting slurry was dried at 70° C., and the X-ray powder diffraction analysis of the resulting powder was made. Only diffraction peaks of zinc oxide and cyanuric acid were detected, and no diffraction peaks of basic zinc cyanurate were detected.

Comparative Example 2

Figure 5:
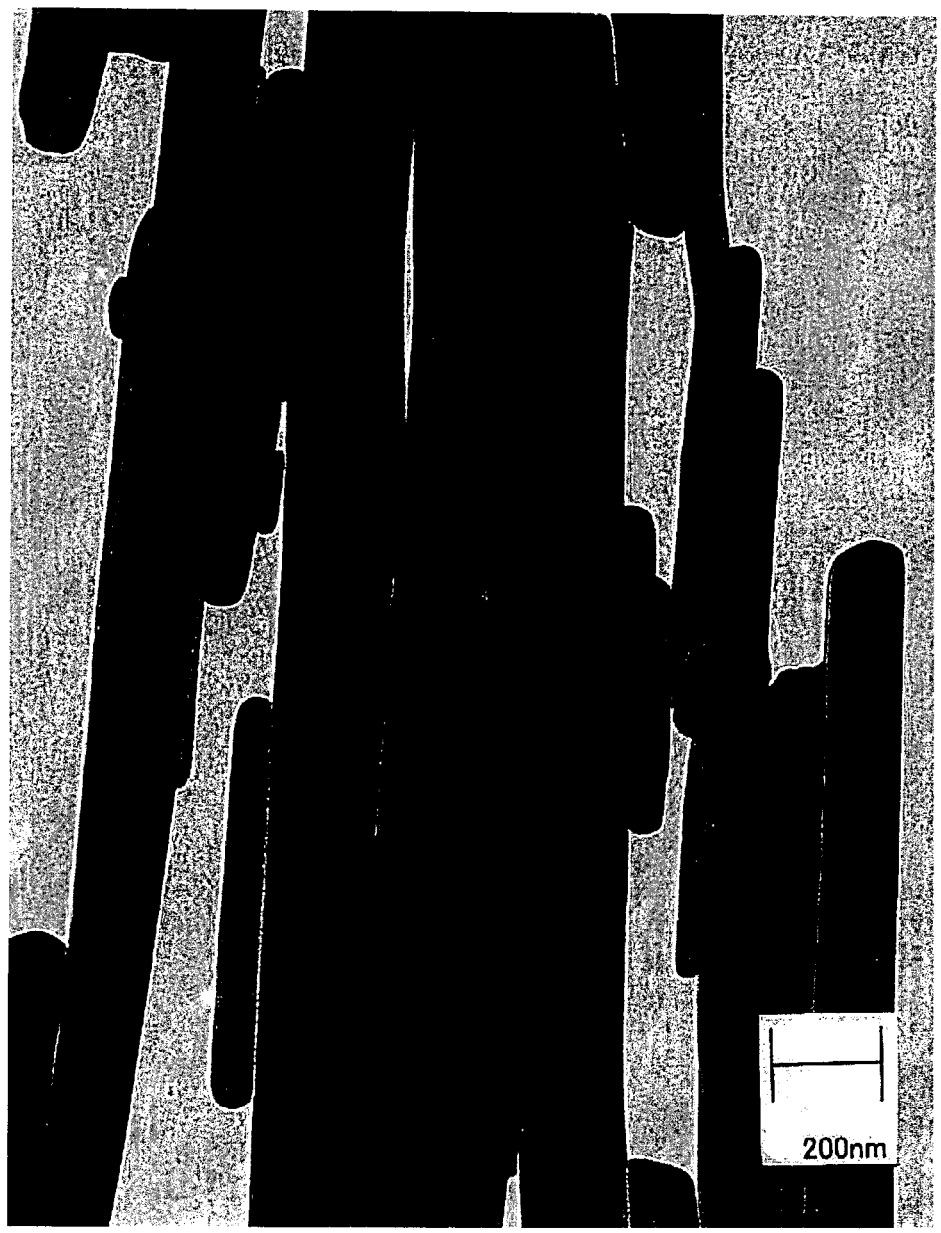
[FIG. 5] is a TEM photograph of Comparative Example 2.

A 1-liter beaker charged with 900 g of pure water was placed on a hot plate equipped with a magnet stirrer, and 18.9 g of a cyanuric acid powder (produced by Nissan Chemical Industries, Ltd.) was charged into the system with stirring by the stirrer. Then, 30.0 g of a zinc oxide powder (JIS-2 grade zinc oxide produced by SAKAI CHEMICAL INDUSTRY CO., LTD.) was charged into the system, and then the mixed slurry was heated to a boil by the hot plate, with stirring using the stirrer. The zinc oxide/cyanuric acid molar ratio was 2.5, and the cyanuric acid concentration with respect to water was 2.1 mass %. After stirring for 8 hours at the 100° C. boil, a white slurry having a pH of 7.1, an electric conductivity of 46 μS/cm, a viscosity of 500 mPa·s, and a solid content when dried at 110° C. of 6.8 mass % was obtained in an amount of 716 g. The X-ray powder diffraction analysis of a 110° C. dried powder of the resulting white slurry showed a diffraction pattern similar to that of Example 1. Fine particles contained in the resulting white slurry comprised basic zinc cyanurate having a major axis length of 2000 to 20000 nm and a minor axis length of 200 to 500 nm according to transmission electron microscopic observation, an average particle diameter $D_{50}$, by the laser diffraction method, of 2620 nm, and a specific surface area Sw, after drying at 70° C., of 5 m²/g. The results are shown in Table 1. A photograph of the fine particles based on transmission electron microscopic observation is shown in FIG. 5.

Comparative Example 3

A batchwise sand grinder container having a volume of 1 L and formed from urethane was charged with 1140 g of stabilized zirconia grinding beads having a diameter of 1 mm, and 300 g of pure water. With the sand grinder container being heated in a hot water bath, a stirring disk was rotated at 1500 rpm, and 5.9 g of a cyanuric acid powder (produced by Nissan Chemical Industries, Ltd.) was charged into the system. Then, with the sand grinder container being heated in the hot water bath, the stirring disk was rotated at 1500 rpm, and 9.3 g of a zinc oxide powder (JIS-2 grade zinc oxide produced by SAKAI CHEMICAL INDUSTRY CO., LTD.) was charged into the system. The zinc oxide/cyanuric acid molar ratio was 2.5, and the cyanuric acid concentration with respect to water was 2.0 mass %. After charging of the zinc oxide powder, the sand grinder container was heated in the hot water bath for 5 hours and, during this process, the stirring disk was rotated at 1500 rpm to disperse the system. The slurry temperature at this time was 60° C. By this treatment, a white slurry having a pH of 7.7, an electric conductivity of 220 μS/cm, and a solid content when dried at 110° C. of 4.8 mass % was obtained in an amount of 300 g. The X-ray powder diffraction analysis of a 110° C. dried powder of the resulting white slurry showed a diffraction pattern similar to that of Example 1. Fine particles contained in the resulting white slurry comprised basic zinc cyanurate having a major axis length of 60 to 120 nm and a minor axis length of 20 to 60 nm according to transmission electron microscopic observation, an average particle diameter $D_{50}$, by the laser diffraction method, of 1500 nm, and a specific surface area Sw, after drying at 70° C., of 27 m²/g. The results are shown in Table 1.

Comparative Example 4

A 500 mL polyethylene wide-mouthed bottle was charged with 300 g of pure water, 4.3 g of a cyanuric acid powder (produced by Nissan Chemical Industries, Ltd.), and 6.7 g of a zinc oxide powder (JIS-2 grade zinc oxide produced by SAKAI CHEMICAL INDUSTRY CO., LTD.). The charge was stirred for 12 hours at a rotational speed of 3000 rpm with the use of a Disper type stirring blade having a diameter of 50 mm. The zinc oxide/cyanuric acid molar ratio was 2.5, and the cyanuric acid concentration with respect to water was 1.4 mass %. The slurry temperature at this time was 35° C. By this treatment, a white slurry having a pH of 7.9, an electric conductivity of 35 µS/cm, and a solid content when dried at 110° C. of 3.5 mass % was obtained. The X-ray powder diffraction analysis of a 110° C. dried powder of the resulting white slurry showed a diffraction pattern similar to that of Example 1. Fine particles contained in the resulting white slurry were agglomerated particles of basic zinc cyanurate having a major axis length of 1000 to 1500 nm and a minor axis length of 50 to 100 nm according to transmission electron microscopic observation, an average particle diameter $D_{50}$, by the laser diffraction method, of 2280 nm, and a specific surface area Sw, after drying at 70° C., of 44 m$^2$/g. The results are shown in Table 1.

Comparative Example 5

A compact crusher (Wander Blender WB-1 produced by OSAKA CHEMICAL CO., LTD.) mounted with a SUS crush cutter blade was charged with 42 g of pure water, 7.1 g of a cyanuric acid powder (produced by Nissan Chemical Industries, Ltd.), and 11.0 g of a zinc oxide powder (JIS-2 grade zinc oxide produced by SAKAI CHEMICAL INDUSTRY CO., LTD.). The cutter blade was rotated for 1 minute at 25000 rpm to crush the charge. The zinc oxide/cyanuric acid molar ratio was 2.5, and the cyanuric acid concentration with respect to water was 16.9 mass %. This procedure was repeated 5 times to obtain a wet white powder. The temperature of this white powder immediately after the procedures was 35° C. The X-ray powder diffraction analysis of this white powder showed a diffraction pattern similar to that of Example 1. The white powder was dispersed in pure water, and observed under a transmission electron microscope. The product was found to have a major axis length of 1000 to 2000 nm and a minor axis length of 60 to 200 nm, an average particle diameter $D_{50}$, by the laser diffraction method, of 20000 nm, and a specific surface area Sw, after drying at 70° C., of 16 m$^2$/g. The results are shown in Table 1.

As shown in Table 1, Examples 1 to 8—in which a mixed slurry formed by blending zinc oxide or basic zinc carbonate, cyanuric acid, and water such that the cyanuric acid concentration was 0.1 to 10.0 mass % with respect to water was subjected to wet dispersion using a dispersion medium at a temperature in the range of 5 to 55° C.—provided fine basic zinc cyanurate having an average particle diameter $D_{50}$, as measured by the laser diffraction method, of 80 to 900 nm, and a specific surface area of 20 to 100 m$^2$/g. Comparative Examples 1 to 3 in which the temperature of wet dispersion was outside the range of 5 to 55° C., and Comparative Examples 4 to 5 in which wet dispersion by shearing, rather than wet dispersion with a dispersion medium, was used, on the other hand, failed in providing fine basic zinc cyanurate having an average particle diameter $D_{50}$, as measured by the laser diffraction method, of 80 to 900 nm, and a specific surface area of 20 to 100 m$^2$/g.

TABLE 1

| | Zn source | Bead mill | Dispersion medium | ZnO/CA (molar ratio) | CA/water (mass %) | Dispersion temp. (°C.) | Specific surface area Sw (m$^2$/g) | Average particle diameter $D_{50}$ (nm) | Major axis length (nm) | Minor axis length (nm) | Axial ratio | pH | Electric conductivity (µS/cm) |
|---|---|---|---|---|---|---|---|---|---|---|---|---|---|
| Ex. 1 | ZnO | sand grinder | stabilized ZrO$_2$ | 2.5 | 2.0 | 9 | 59 | 103 | 100-200 | 10-15 | 12 | 7.1 | 84 |
| Ex. 2 | ZnO | sand grinder | stabilized ZrO$_2$ | 2.5 | 2.0 | 16 | 49 | 155 | 100-300 | 10-20 | 13 | 7.1 | 109 |
| Ex. 3 | ZnO | sand grinder | stabilized ZrO$_2$ | 2.5 | 2.0 | 23 | 32 | 175 | 100-400 | 20-30 | 10 | 7.0 | 120 |
| Ex. 4 | ZnO | sand grinder | stabilized ZrO$_2$ | 2.5 | 3.2 | 40 | 26 | 188 | 100-300 | 20-30 | 8 | 6.8 | 148 |
| Ex. 5 | ZnO | sand grinder | stabilized ZrO$_2$ | 2.5 | 2.0 | 50 | 25 | 623 | 100-200 | 20-40 | 5 | 8.2 | 176 |
| Ex. 6 | basic zinc carbonate | sand grinder | stabilized ZrO$_2$ | 2.5 | 1.4 | 30 | 30 | 303 | 100-300 | 20-40 | 8 | 6.3 | 556 |
| Ex. 7 | ZnO | pearl mill | stabilized ZrO$_2$ | 2.5 | 0.7 | 32 | 51 | 310 | 100-600 | 25-50 | 9 | 6.8 | 67 |
| Ex. 8 | ZnO | sand grinder | stabilized ZrO$_2$ | 3.0 | 2.0 | 23 | 40 | 152 | 100-300 | 15-20 | 11 | 7.8 | 98 |
| Comp. Ex. 1 | ZnO | beaker | magnet stirrer | 2.5 | 2.1 | 70 | — | — | Unreacted | — | — | — | — |
| Comp. Ex. 2 | ZnO | beaker | magnet stirrer | 2.5 | 2.1 | 100 | 5 | 2620 | 2000-20000 | 200-500 | 30 | 7.1 | 46 |
| Comp. Ex. 3 | ZnO | sand grinder | stabilized ZrO$_2$ | 2.5 | 2.0 | 60 | 27 | 1500 | 60-120 | 20-60 | 2 | 7.7 | 220 |
| Comp. Ex. 4 | ZnO | Disper dispersion | Disper blade (shearing) | 2.5 | 1.4 | 35 | 44 | 2280 | 1000-1500 | 50-100 | 17 | 7.9 | 35 |
| Comp. Ex. 5 | ZnO | blender | cutter blade (shearing) | 2.5 | 16.9 | 35 | 16 | 20000 | 1000-2000 | 60-200 | 12 | — | — |

Applied Example 1

The 110° C. dried powder (40 mg) of the basic zinc cyanurate obtained in Example 7, and 4.0 g of polylactic acid resin (NW3001D, number average molecular weight 72,000, melting point 164° C.; produced by NatureWorks LLC) were charged into a kneader (LABO PLASTOMILL, TOYO SEIKI CO., LTD.) heated to 185° C., and the charge was kneaded for 5 minutes at 50 rpm. After cooling, the kneaded resin was withdrawn, and sandwiched between a Teflon (registered trademark) sheet and a brass plate. The resulting composite was placed in a hot pressing machine having an upper part and a lower part both heated at 185° C., and was pressurized at 0.5 kgf so as to form a 0.4 mm thick film, whereby such a film was prepared. The resulting film sample-shaped was cut to a small piece, which was subjected to the following DSC measurement (using DSC-200 produced by Seiko Instruments Inc.): The sample piece was heated up to 200° C. at a rate of 100° C./min, held as such for 5 minutes, and then cooled at a rate of 5° C./min. Based on the apex of an exothermic peak due to the crystallization of polylactic acid observed during cooling, the crystallization temperature Tc was measured. The results are shown in Table 2. The visible light transmission of the resulting film was measured with a color difference meter (TC-1800MK, produced by Tokyo Denshoku Co., Ltd.). The results are also shown in Table 2.

Applied Comparative Example 1

The same procedure as in Applied Example 1 was performed, except that the basic zinc cyanurate obtained in Comparative Example 2 was used instead of using the basic zinc cyanurate obtained in Example 7.

Applied Comparative Example 2

The same procedure as in Applied Example 1 was performed, except that no basic zinc cyanurate was added to the polylactic acid resin.

Applied Example 2

The 110° C. dried powder (36 mg) of the basic zinc cyanurate obtained in Example 7, and 3.6 g of polypropylene resin (NOVATEC-PP MA3, number average molecular weight 111,000, melting point 165° C.; produced by Japan Polychem Corporation) were charged into a kneader (LABO PLASTOMILL, TOYO SEIKI CO., LTD.) heated to 185° C., and the charge was kneaded for 5 minutes at 50 rpm. After cooling, the kneaded resin was withdrawn, and sandwiched between a Teflon sheet and a brass plate. The resulting composite was placed in a hot pressing machine having an upper part and a lower part both heated at 185° C., and was pressurized at 0.5 kgf so as to form a 0.4 mm thick film, whereby such a film was prepared. This film-shaped sample was cut to a small piece, which was subjected to the following DSC measurement (using DSC-200 produced by Seiko Instruments Inc.): The sample piece was heated up to 200° C. at a rate of 100° C./min, held as such for 5 minutes, and then cooled at a rate of 5° C./min. Based on the apex of an exothermic peak due to the crystallization of polypropylene observed during cooling, the crystallization temperature Tc was measured. The results are shown in Table 2. The visible light transmission of the resulting film was measured with a color difference meter (TC-1800MK, produced by Tokyo Denshoku Co., Ltd.). The results are also shown in Table 2.

Applied Comparative Example 3

The same procedure as in Applied Example 2 was performed, except that the basic zinc cyanurate obtained in Comparative Example 2 was used instead of using the basic zinc cyanurate obtained in Example 7.

Applied Comparative Example 4

The same procedure as in Applied Example 2 was performed, except that no basic zinc cyanurate was added to the polypropylene resin.

As a result, as shown in Table 2, the crystallization temperature was found to be raised by adding basic zinc cyanurate, demonstrating that basic zinc cyanurate could be used as a crystal nucleating agent for resin. The basic zinc cyanurate of Example 7 was remarkably smaller particles than in Comparative Example 2. Thus, in Applied Example 1 and Applied Example 2 using Example 7, the visible light transmission was higher than in Applied Comparative Example 1 and Applied Comparative Example 3 using Comparative Example 2.

TABLE 2

| Basic zinc cyanurate | Resin | Basic zinc cyanurate powder concentration (mass %) | Crystallization temperature Tc (° C.) | Visible light transmission (%) |
|---|---|---|---|---|
| Applied Ex. 1 | Polylactic acid | 1.0 | 121 | 32 |
| Applied Comp. Ex. 1 | Polylactic acid | 1.0 | 120 | 23 |
| Applied Comp. Ex. 2 | Polylactic acid | 0 | 114 | 39 |
| Applied Ex. 2 | Polypropylene | 1.0 | 129 | 33 |
| Applied Comp. Ex. 3 | Polypropylene | 1.0 | 129 | 24 |
| Applied Comp. Ex. 4 | Polypropylene | 0 | 123 | 45 |

The invention claimed is:

1. Basic zinc cyanurate fine particles, having an average particle diameter $D_{50}$, as measured by a laser diffraction method, of from 80 to 900 nm and a specific surface area of from 20 to 100 $m^2/g$,
    wherein the particles have a primary particle diameter, as observed under a transmission electron microscope, of from 100 to 800 nm on a major axis and a diameter of from 10 to 60 nm on a minor axis, wherein a ratio between the major axis and the minor axis is 5 to 25.

2. The basic zinc cyanurate fine particles according to claim 1, wherein the particles are produced by subjecting a mixed slurry to a wet dispersion with a dispersion medium at a temperature in a range of from 5 to 55° C., wherein the mixed slurry is formed by blending water, cyanuric acid, and at least one component selected from the group consisting of a zinc oxide and a basic zinc carbonate, wherein a cyanuric acid concentration is 0.1 to 10.0 mass % with respect to water.

3. A method for producing basic zinc cyanurate fine particles according to claim 1, the method comprising subjecting a mixed slurry to a wet dispersion with a dispersion medium at a temperature in a range of from 5 to 55° C., wherein the mixed slurry is formed by blending water and cyanuric acid, wherein a cyanuric acid concentration is 0.1 to 10.0 mass % with respect to water, and further blending at least one component selected from the group consisting of a zinc oxide and a basic zinc carbonate.

4. The method according to claim 3, wherein the basic zinc cyanurate fine particles have an average particle diameter $D_{50}$, as measured by a laser diffraction method, of from 80 to 900 nm and a specific surface area of from 20 to 100 $m^2/g$.

5. The method according to claim 3, wherein the dispersion medium is at least one medium selected from the group consisting of stabilized zirconia beads, vitreous silica beads, soda-lime glass beads, and alumina beads, wherein each bead has a diameter of from 0.1 to 10 mm.

6. The method according to claim 4, wherein the dispersion medium is at least one medium selected from the group consisting of stabilized zirconia beads, vitreous silica beads, soda-lime glass beads, and alumina beads, wherein each bead has a diameter of from 0.1 to 10 mm.

7. The method according to claim 3, wherein the cyanuric acid concentration is 0.1 to 5.0 mass %, with respect to water.

8. The method according to claim 3, wherein a molar ratio between zinc oxide or basic zinc carbonate and cyanuric acid is 1.0 to 5.0.

9. The method according to claim 3, wherein a molar ratio between zinc oxide or basic zinc carbonate and cyanuric acid is 2.0 to 3.0.

10. The method according to claim 5, wherein the dispersion medium is stabilized zirconia beads.

11. The method according to claim 5, wherein each bead has a diameter of 0.5 to 2.0 mm.

12. The method-according to claim 3, wherein the basic zinc cyanurate fine particles have an average particle diameter $D_{50}$, as measured by a laser diffraction method, of from 100 to 500 nm and a specific surface area of from 30 to 80 $m^2/g$.

13. The basic cyanurate fine particles according to claim 1, wherein the particles are acicular or plate-shaped.

14. The basic cyanurate fine particles according to claim 1, wherein the particles are elongated.

15. The basic zinc cyanurate fine particles according to claim 1, wherein the particles are a corrosion inhibiting coating agent.

16. The basic zinc cyanurate fine particles according to claim 1, wherein the particles are a crystal nucleating agent that controls the crystallinity of a crystallizable polymer.

17. The basic zinc cyanurate fine particles according to claim 15, wherein the crystallizable polymer is one selected from the group consisting of a polypropylene, a polylactic acid, and a polyethylene.

18. The basic zinc cyanurate fine particles according to claim 1, wherein the particles are a polymeric material filler.

* * * * *